(12) United States Patent
Sands et al.

(10) Patent No.: US 6,403,530 B1
(45) Date of Patent: Jun. 11, 2002

(54) CARRIER METHODOLOGY FOR AERIAL DISPERSAL AND SOIL PENETRATION OF BIOACTIVE AGENTS

(75) Inventors: David C. Sands, Bozeman, MT (US); Kanat S. Tiourebaev, Almaty (KZ); Alice L. Pilgeram; Timothy W. Anderson, both of Bozeman, MT (US)

(73) Assignee: Ag/Bio Con, Inc., Bozeman, MT (US)

( * ) Notice: Subject to any disclaimer, the term of this patent is extended or adjusted under 35 U.S.C. 154(b) by 0 days.

(21) Appl. No.: 09/748,501

(22) Filed: Dec. 20, 2000

Related U.S. Application Data

(60) Provisional application No. 60/172,772, filed on Dec. 20, 1999.

(51) Int. Cl.[7] ............ A01N 3/02; A01N 63/00; A01N 25/26
(52) U.S. Cl. .......... 504/116; 504/100; 504/117
(58) Field of Search ............... 504/100, 117, 504/116

(56) References Cited

FOREIGN PATENT DOCUMENTS

| GB | 2110518 | * 6/1983 |
|---|---|---|
| WO | 9959412 | * 11/1999 |

* cited by examiner

*Primary Examiner*—Alton Pryor
(74) *Attorney, Agent, or Firm*—Klarquist Sparkman, LLP

(57) ABSTRACT

We herein reveal a methodology for the dispersal of bioherbicides intended for control of target plants. The methodology can be used for dispersal of various bioactive agents in addition to bioherbicides, for instance to disseminate bioassistive agents such as Rhizobium cultures. We describe a process for selection of live seed carriers, bioherbicide coating of selected seed, and aerial dispersion of live seed formulation. Aerial dispersion of bioherbicide with live seed carriers demonstrates a vast improvement in bioherbicide establishment, including penetration throughout the soil profile and into the target root zone. In addition, the active concentration of the bioherbicide is increased within the root zone of the carrier plant. This novel approach for dispersal of bioherbicides can be used across a wide spectrum of target plants and should greatly improve the efficacy of bioherbicides.

22 Claims, No Drawings

CARRIER METHODOLOGY FOR AERIAL DISPERSAL AND SOIL PENETRATION OF BIOACTIVE AGENTS

This application claims the benefit of Provisional Application No. 60/172,772 filed Dec. 20, 1999.

STATEMENT REGARDING FEDERALLY SPONSORED RESEARCH

The United States Government may have certain rights in this application pursuant to a non-competitive ARS Grant No. 58-1275-5-013, awarded by the USDA.

INTRODUCTION

Fusarium wilt was reported to cause serious loss in the cultivated hemp crop *Cannabis sativa* in Italy (Noviello and Snyder, 1962). Due to its restricted host range this pathogen was proposed as a potential biocontrol agent for unwanted *C. sativa* (McCain and Noviello, 1984). Although this species shows promise as a biocontrol candidate, significant problems with effectively inoculating target species have been encountered by Fusarium researchers (Kraft and Haglund, 1978; Armstrong and Armstrong, 1981). In addition, these pathogens can be sensitive to numerous environmental factors, such as temperature, relative humidity, rainfall, etc.

Improving the delivery of the pathogen to the target plant could increase the kill rate of the mycoherbicide. Downward movement of the mycoherbicide from the soil surface into the rhizosphere limits the success of soil-borne biocontrol agents. To overcome these limitations, we evaluated the effectiveness of using live plant seeds coated with fungal spores as a delivery system for the mycoherbicide. *Fusarium oxysporum* f. sp. cannabis is nonpathogenic on plant species other than Cannabis. However, the pathogen will successfully grow on the root surface of nonhost plant as a saprophyte. Thus, as non-host seed coated with *F. oxysporum* f. sp. cannabis germinates and sends roots into the soil, the Fusarium multiplies, continues to colonize emerging tissue, and is carried further into the soil. This root growth effectively distributes the fungus through the soil environment, where it can contact the target host tissue and cause disease. An added benefit of live seed formulations, besides their ability to effectively deliver pathogens, is the ability to introduce a reclamation plant species as part of the treatment.

MATERIALS AND METHODS

Fungal cultures and preservation. *Fusarium oxysporum* f. sp. cannabis strains were isolated from diseased *Cannabis sativa* plants in the Chu River Valley, Djambil Region, Kazakhstan, from 1995 to 1996.

Marking of fungal strains. Chlorate resistant mutants were selected to facilitate positive identification of our mycoherbicidal fungi (Correll et al. 1987; Hadar et al. 1989). Colonies showing wild type growth on media containing chlorate were isolated and characterized on minimal media containing sodium nitrate, sodium nitrite, or hypoxanthine as the sole nitrogen source. An auxotroph of strain Cs95 lacking nitrate dehydrogenase (nit 1) was selected for further analysis.

Fungal spore suspension. Fungal cultures were grown in 0.5 L flasks containing 200 ml PDB (Difco) for 7–10 days on a shaker (200 rpm) at ambient temperature, until a concentration of $10^8$ microconidia/ml was achieved. The liquid cultures were filtered through 4 layers of cheesecloth and the final spore concentration was adjusted to $10^7$ sp/ml with additional sterile water.

Test plants and seeds. The seeds used during this experiment were *C. sativa* (var. Afghan), *Festuca arundinaceae* (var. Apache), *Agropyron spicatum*, and *Lycopersicon esculentum* (cv. Bonnie Best). The seeds of selected plant species were surface sterilized in a 0.5% sodium hypochlorite solution for 3 minutes, rinsed with sterile distilled $H_2O$ and dried in a laminar flow hood.

Inoculum Production.

Canola flour mix. Canola Flour Mix (CFM) employed in greenhouse studies was prepared by combining equal parts ground canola flour and wheat flour with 1% by volume activated charcoal and enough water amended with 0.01% Silwet L-77 surfactant to make the mixture stick together. This formulation is very effective in greenhouse studies, but is fairly labor intensive and expensive to produce. The spore suspension ($10^7$ spores/ml) is added to the formulations at a rate of 10 ml of spore suspension/100 grams of carrier. This mixture is air dried under a laminar flow hood for 4–6 hours and stored in sealed paper bags.

Birch sawdust formulation. Birch sawdust formulation (BSF) involves a readily available and inexpensive carrier and it was effectively formulated by coating 100 g of birch sawdust with 50 milliliters of a 0.1% yeast extract and 1 M citric acid solution (pH 5.5). This formulation was well mixed and then autoclaved. The spore suspension ($10^7$ spores/ml) was added to the formulations at a rate of 10 ml of spore suspension/100 grams of carrier. This mixture was air dried under a laminar flow hood for 4–6 hours and stored in sealed paper bags.

Live seed formulation. Live seed formulations (LSF) of *C. sativa* and nonhost seeds *Festuca arundinaceae* (var. Apache), *Agropyron spicatum*, and *Lycopersicon esculentum* (cv. Bonnie Best) were prepared following the protocol described by Grey and Mathre (1988). One hundred seeds of each plant sp. were surface sterilized in a 0.5% NaOCl solution for 3–5 min, then immersed into different coating solutions, stirred, and allowed to air dry in a laminar flow hood for 1–2 hours. Coating agents used were 5% carboxymethyl cellulose (CMC), 2% methyl cellulose (MC), Mycotech oil (Oil) and liquid Potato Dextrose Broth spore suspension (SS). After drying, the coated seeds were allowed to soak in 10 ml of a conidia suspension ($10^7$ spores/ml) of *F. oxysporum* f. sp. cannabis for 10 minutes. The coated seeds were then air dried for 24 hours and stored at 4° C.

To determine the fungal spore concentration per seed, 10 seeds from each treatment were placed into 1 ml of sterile $H_2O$, shaken for 5 min and the resulting spore suspension was counted with a hemacytometer (4 DF, Neubauer 0.1 mm). The test included five treatments with replication (n=5). The mean fungal spore concentrations per seed were obtained and data were analyzed in a completely randomized design, with five replications per treatment.

Colonization of *C. sativa* seedlings by *F. oxysporum* f. sp. cannabis. The ability of *F. oxysporum* f. sp. cannabis to colonize emerging root tissue of the host seedlings was examined. Live seed formulation of *C. sativa* seeds was prepared as described above using CMC and a spore suspension of *Fusarium oxysporum* f. sp. cannabis isolates Cs72, Cs109-2, and Cs95. Coated pre-germinated Cannabis seeds were then placed on water agar plates, three plates per treatment. Each plate contained ten seeds, for a total of 30 seeds per treatment. One week after incubation at ambient temperature, ten seedlings from each treatment of similar root length were selected for spore concentration assessment. The chosen seedlings were washed with 50 ml of dH$_2$O. The mean fungal spore concentration per seed was determined by dilution plating on Komada's medium (Komada, 1975). Each colonization experiment was performed three times.

Analysis of the depth and concentration of Fusarium spores. The effect of formulation on the downward movement of *Fusarium oxysporum* f. sp. cannabis Cs95 through a soil profile was examined using the following system. Five-ml plastic pipettor tips (15 cm—length, 1 cm—diameter) were filled with Montana State University Plant Growth Center (PGC) soil mix amended with the wetting agent Aqua-Gro 2000. The soil columns were placed into 25 ml glass test tubes, covered with plastic caps and sterilized with two autoclaving cycles (60 minutes, 120° C.). Four ml of sterile water was added aseptically to each soil column and allowed to equilibrate, and excess water was allowed to drain off. No more water was added during the experiment. This system allows plant seedlings to grow for more than two weeks in sterile conditions without watering. This allowed us to exclude movement of the fungal spores facilitated by added water. The soil columns were inoculated with different formulations of a nitrate non-utilizing mutant (nit-1) of *F. oxysporum* f. sp. cannabis strain Cs95. The inoculum formulations used in this experiment were: live seed formulation (*Cannabis sativa*), food-based formulation (CFM), and liquid spore suspension. In treatments using live seed formulation, each individual soil column was inoculated with a single coated seed. The concentration of *Fusarium oxysporum* microconidia on each seed was approximately 10$^4$ spores. The spore concentration on the food-based formulation, CFM, was adjusted to the same spore concentration per tube. In the treatment with liquid spore suspension the top of the soil column was infested with 20 µl of 10$^6$ spores/ml suspension. Sterile seeds of *C. sativa* coated in CMC were used in the control treatment. The soil columns were then placed inside glass test tubes, covered with plastic caps and incubated at 28° C. (19 hours light/5 hours dark). The space between the plastic cap and soil surface provided enough room for seedlings to grow for 10 days after germination. Ten days after germination, the soil columns were cut into 1 cm segments, which contained 1 g of wet soil. Soil segments were serially diluted PDA plates containing 3% chlorate The roots in all soil columns tested reached a depth of 9 cm at the end of the experiment. The experiment was conducted in autoclaved and non autoclaved soil and repeated once. Each experiment contained four treatments with replication (n=5). *Fusarium oxysporum* was not recovered from the control treatments, which were not included in the data analysis. The mean fungal concentration was estimated and data was analyzed as a factorial with soil depth and inoculum as two factors in a completely randomized design with five replications per treatment.

A similar experiment examined the effect of different live seed formulations. The nitrate non-utilizing mutant of *Fusarium oxysporum* f. sp. cannabis Cs95 (nit-1) was formulated onto the live host seeds of *Cannabis sativa*, Bluebunch wheatgrass and tomato. The experiment involved the following treatments: 1) Cs95 coated Cannabis seeds, 2) Cs95 coated Bluebunch wheatgrass, 3) Cs95 coated tomato seeds, 4) sterile control, 5) liquid Cs95 spore suspension, 6) Cs95 CFM, and 7) autoclaved CFM. Each treatment was applied to 5 soil columns assigned in complete randomized fashion. The experiment was repeated once. Soil dilution data from the sterile control treatment were not included in the data analysis. The mean fungal concentration was estimated and data were analyzed as a factorial with soil depth and inoculum as two factors in a completely randomized design with five replications per treatment.

Field studies of live seed formulations. Field plots to determine the effectiveness of live seed formulations of *F. oxysporum* f. sp. cannabis strain Cs95 were established at the Kazakh Institute of Agriculture Experiment Station, Academy of Agriculture, Republic of Kazakhstan. Viable *Festuca arundinaceae* seeds were chosen as a seed carrier due to their availability, their high germination rate and because this plant species is already present in the region. *Festuca arundinaceae* is also adapted to a wide variety of soils, from highly acid to highly alkaline (Wheeler and Hill, 1957).

Field testing of the performance of the live seed formulations involved two experiments. In one experiment, inoculations of experimental plots (1 m$^2$) were performed prior to the planting of Cannabis. The following treatments were included: 1) live seed formulation (*Festuca arundinaceae*) coated with Cs95 (LSFf), 2) *F. arundinaceae* without Cs95, 3) birch sawdust formulation, 4) autoclaved Birch sawdust formulation, and 5) non treated. Each treatment was applied to three experimental plots. After the *F. arundinaceae* seeds germinated (about one week after inoculation), the experimental plots were seeded with 100 *C. sativa* seeds. Upon germination *C. sativa* seedlings were thinned down to 20 plants per plot.

In the second experiment, inoculations were performed on established Cannabis plots. The experiment included the following treatments: 1) live seed formulation (*Festuca arundinaceae*) coated with Cs95 (LSFf), 2) *F. arundinaceae* without Cs95, 3) birch sawdust formulation, 4) autoclaved birch sawdust formulation and 5) non treated. Each treatment was applied in a completely randomized fashion to three 1 m$^2$ plots containing 20 *C. sativa* seedlings. Plants were inoculated at the 2–3 pair of true leaves stage.

The average disease ratings of the Cannabis plants in the field experimental plots were obtained and data from each experiment were analyzed separately in a completely randomized design with three replicates per treatment. Analysis of variance was performed using the SAS program. To compare differences between more than two treatment means, least significant differences were calculated at α=5%.

Evaluation of *Cannabis sativa* plants affected by Fusarium wilt. Individual plants were rated for disease severity on a scale of 1 to 5, where 1=no disease, 2=minor wilting of lower leaves, 3=wilting symptoms observed on 25–50% of leaves, 4=>75% leaves show severe wilting symptoms, 5=dead plant.

Disease Incidence Percent was estimated for each treatment as %=a/b×100, where a=number of *C. sativa* plants with severe disease symptoms (ratings 3 through 5) and b=total number of *C. sativa* plants per treatment.

RESULTS

Evaluation of coating agents for live seed carriers.

The choice of the coating agent depended on its ability to hold fungal spores on the seed surface. The CMC coating was chosen over methyl cellulose (MC), Mycotech oil (Oil) and liquid Potato Dextrose Broth spore suspension (SS) (Table 1).

TABLE 1

Mean Fungal Spore Concentration on Seeds Coated with Different Coating Agents.

| Coating Agent | Cannabis seed log spores/ml | Tomato seed log spores/ml | grass seed log spores/ml |
|---|---|---|---|
| Control | 0 a[1] | 0 a | 0 a |
| Spore suspension | 4.39 bc | 4.27 b | 4.78 d |
| Mycotech oil | 4.60 cd | 5.25 e | 5.30 e |
| Methyl cellulose | 4.81 d | 4.78 d | 5.49 e |
| Carboxymethyl cellulose | 5.38 e | 5.52 e | 5.34 e |
| LSD (0.05) 0.309 | | | |

[1]Values are means of 5 replicates, and values followed by the same letter are not significantly different at $p < 0.05$. Ten seeds from each treatment were placed into 1 ml of sterile $H_2O$, shaken for 5 minutes and the resulting spore suspension was counted with a hemacytometer.

Colonization of *C. sativa* Seedlings by *F. oxysporum* f. sp. cannabis

*Fusarium oxysporum* f. sp. cannabis initially colonized emerging root tissue of *C. sativa* without killing the plant seedlings. The final concentration of *F. oxysporum* f. sp. cannabis on germinated tissue was compared to the applied concentration (Table 2). The increase in propagule numbers on emerging root tissues was up to 10,000 fold.

TABLE 2

Increase in *Fusarium oxysporum* f. sp *cannabis* on Emerging Root Tissue of *Cannabis sativa* Seedlings.

| Strain | Initial | Final | Increase |
|---|---|---|---|
| Control | 0 | 0 | 0 |
| Cs95 | $10^4$ | $10^8$ | 10,000x |
| Cs109-2 | $10^4$ | $10^8$ | 10,000x |
| Cs72 | $10^4$ | $10^6$ | 100x |

Analysis of the Distribution of Fusarium Spores Throughout a Soil Profile

When the pathogen was applied as a liquid spore suspension, downward movement of the pathogen in a soil column without any additional water was limited to 3 cm (FIG. 1). When the pathogen was applied as a granular food based formulation (CFM), fungal spores could be detected in the soil to a depth of 5 cm, but the spore concentration was decreased about three logs relative to the applied concentration. However, when the pathogen was applied in the form of live seed formulation, it was present on the entire length of the root as it grew into the soil. The propagule concentration did not increase as it descended, but rather maintained a relatively constant spore concentration along the entire root length. These results suggest that movement of the pathogen in the soil was facilitated by the root growth of the host plant. In addition, the live seed formulation resulted in significantly higher propagule concentration than the Food based formulation at increasing depths of the soil columns filled either with autoclaved (Table 3) or non-autoclaved soil (Table 4).

TABLE 3

Movement of *F. oxysporum* f. sp. *cannabis* Isolate Cs95 (nit-1) in Soil Columns (Autoclaved Soil)

| | Concentration of *F. o. c.* in a soil column cfu/g (log) | | | | |
|---|---|---|---|---|---|
| Treatment[1] | 1 cm | 3 cm | 5 cm | 7 cm | 9 cm |
| Control | 0 a[2] | 0 a | 0 a | 0 a | 0 a |
| Ss | 5.7 de | 4.42 c | 0 a | 0 a | 0 a |
| CFM | 5.91 e | 4.52 c | 2.47 b | 0 a | 0 a |
| LSF | 5.64 de | 4.82 cd | 4.71 c | 4.37 c | 3.91 b |

[1]Control = *C. sativa* seeds coated with carboxymethyl cellulose (sterile control). ss = liquid spore suspension. CFM = canola flour mix inoculum. LSFcs = *C. sativa* live seed formulation.
[2]Values are means of 5 replicates; data were log transformed prior to analysis, and values followed by the same letter are not significantly different at $p < 0.05$.

TABLE 4

Movement of *F. oxysporum* f. sp. *cannabis* Isolate Cs95 (nit-1) in Soil Columns (Non-autoclaved Soil)

| | Concentration of *F. o. c.* in a soil column cfu/g (log) | | | | |
|---|---|---|---|---|---|
| Treatment[1] | 1 cm | 3 cm | 5 cm | 7 cm | 9 cm |
| Control | 0 a2 | 0 a | 0 a | 0 a | 0 a |
| Ss | 5.56 e | 4.06 c | 0 a | 0 a | 0 a |
| CFM | 5.59 e | 4.15 c | 1.91 b | 0 a | 0 a |
| LSF | 5.68 e | 4.69 d | 4.22 cd | 4.04 c | 3.76 c |
| LSD (.05) 0.539 | | | | | |

[1]Control = *C. sativa* seeds coated with carboxymethyl cellulose (sterile control). ss = liquid spore suspension. CFM = canola flour mix inoculum. LSFcs = *C. sativa* live seed formulation.
[2]Values are means of 5 replicates, data were log transformed prior to analysis, and values followed by the same letter are not significantly different at $p < 0.05$.

Effect of Live Seed Formulations on Movement of the Mycoherbicide

In the treatments when *F. oxysporum* Cs95 was applied in the form of live seed formulation using bluebunch wheat grass, the pathogen was recovered from soil at the same depth as when applied to *C. sativa* (Table 5).

However the concentration of the recovered mycoherbicide was significantly less than in the case of bluegrass than *C. sativa* ($p<0.05$).

TABLE 5

Movement of *F. oxysporum* f. sp. *cannabis* Isolate Cs95 (nit-1) in Soil Columns Facilitated by Roots of Host and Non-host Plants in Nonautoclaved Soil.

| | | Concentration of *F. o. c.* cfu/g (log) | | | | |
|---|---|---|---|---|---|---|
| Treatment[1] | Carrier Seed | 1 cm | 3 cm | 5 cm | 7 cm | 9 cm |
| Control | — | 0 a | 0 a | 0 a | 0 a | 0 a |
| Ss | — | 5.65 i | 3.7 fe | 0 a | 0 a | 0 a |
| 5CFM | — | 5.75 i | 4.36 fg | 0.10 a | 0 a | 0 a |
| LSFcs | *C. sativa* | 5.63 i | 4.77 hg | 4.45 g | 4.27 fe | 3.59 e |
| LSFbwg | Bluegrass | 5.18 hi | 2.59 d | 2.49 cd | 2.53 dc | 1.06 b |
| LSFt | Tomato | 4.69 hg | 1.86c | 1.06 b | 0.49a | 0 a |
| LSD (.05) 0.71 | | | | | | |

[1]Control = *C. sativa* seeds, as well as bluebunch wheatgrass and tomato seeds, were coated with carboxymethyl cellulose (sterile control). ss = liquid spore suspension. CFM = canola flour mix inoculum. LSFcs = *C. sativa* live seed formulation. LSFbwg = bluebunch wheatgrass live seed formulation. LSFt = tomato live seed formulation.

TABLE 5-continued

Movement of *F. oxysporum* f. sp. *cannabis* Isolate Cs95 (nit-1) in Soil Columns Facilitated by Roots of Host and Non-host Plants in Nonautoclaved Soil.

| Treatment[1] | Carrier Seed | Concentration of *F. o. c.* cfu/g (log) | | | | |
|---|---|---|---|---|---|---|
| | | 1 cm | 3 cm | 5 cm | 7 cm | 9 cm |

[2]Values are means of 5 replicates; data were log transformed prior to analysis. Values followed by the same letter are not significantly different at $p < 0.05$.

Field Studies

The live seed formulation consisting of *C. sativa* coated with *F. oxysporum* f. sp. cannabis resulted in higher levels of disease incidence in both field experiments (Table 6). The food based formulation (birch sawdust) induced 30% disease in the plots that were inoculated after *C. sativa* was established and 28.3% disease in plots inoculated before *C. sativa* was planted. The live seed formulation resulted in approximately 50% more disease than the birch sawdust formulation.

TABLE 6

Disease Severity in *Cannabis sativa* Plants Grown in Field Soil Infested with Different Inoculum Formulations of *F oxysporum* f. sp. *cannabis* isolate Cs95.

| | A Inoculation after planting | | B Inoculation before planting | |
|---|---|---|---|---|
| Treatment | DAI[4] | % disease[6] | DAI | % disease |
| LSF sterile[1] | 1.30 b[5] | 1.8% | 1.23 a | 0% |
| LSF | 2.70 d | 48.3% | 2.52 c | 41.7% |
| BSF sterile[2] | 1.08 a | 0% | 1.13 a | 0% |
| BSF | 2.12 c | 30% | 1.98 b | 28.3% |
| Control[3] | 1.05 a | 0% | 1.10 a | 0% |
| LSD (0.05) | 0.264 | | 0.275 | |

[1]Live seed formulation without pathogen.
[2]Food based formulation autoclaved.
[3]Uninoculated *C. sativa* plants.
[4]Means of Disease Average Indexes. Disease Average Index was rated using a 1 to 5 rating scale for each of three experimental plots within each treatment. See text for details.
[5]Means with the same letter are not significantly different ($p < 0.05$).
[6]Means of Percent Disease. Percent Disease was estimated for each of three experimental plots within each treatment. Percent Disease = a/b × 100, where a number of *C. sativa* plants with disease symptoms per plot, and b total number of *C. sativa* plants per plot.

DISCUSSION

In field tests in Kazakhstan during the summers of 1996 and 1997, about 35% of Cannabis plants in experimental plots treated with a sawdust formulation of *F. oxysporum* f. sp. cannabis died or exhibited severe wilt symptoms (Tiourebaev, et al., 1998). We believe that the performance of the biocontrol agent could be improved by using other inoculation methods. In the case of most root pathogens, their effectiveness depends on successful soil penetration toward the root zone (Ben-Yephet et al. 1994).

We compared downward movement of the mycoherbicide in the soil columns when applied in different formulations. Recently, Grazia-Garza (1998) studied the effect of water percolation on movement of *Fusarium oxysporum* propagules in soil columns. He showed that, in general, 10 fold fewer cfu were recovered at 8–10 cm depth compared to a 0–2 cm depth. The effect of water on downward movement of fungal propagules in most of the soils depended on the amount of water added (Hepple, 1960). However, in semi-arid regions with low annual precipitation such as the Chu River Valley it would be hard to rely on passive transport of the mycoherbicide by water. In our study, we were able to compare downward movement of fungal propagules in soil columns without any water added. Our study indicated that *Fusarium oxysporum* f. sp. cannabis propagule density declined in the top 3–5 cm of the soil column when applied in the form of food based formulation, both in autoclaved and nonautoclaved soils. In both CFM and SS treatments, most of the cfu were recovered from the top 1–3 cm of the column ($p<0.05$) (Table 3, 4, & 5). Live seed formulation proved to be superior to other tested formulations. The propagules of the mycoherbicide could be recovered from significantly deeper soil and at significantly higher numbers when applied as live seed formulation as compared to the tested food based formulations. Due to the ability of *Fusarium oxysporum* to grow saprophytically on non-host tissues, the mycoherbicide can be applied at lower rates when live seed formulation is used. Initial pathogen concentration can be reduced $10^3$–$10^4$ times. This could be important for large scale application of mycoherbicides, both in terms of the cost and the reduction of the impact of introduced microorganisms on soil microflora.

The change in fungal spore concentration below the soil surface varied depending on which carrier seed was used for the live seed formulation. This suggests that more efficacious carrier seed/seedling systems may yet be discovered.

The average disease ratings of *Cannabis sativa* plants in the field experimental plots inoculated with the live seed formulation of *Fusarium oxysporum* were significantly higher than in plots inoculated with food based formulation. In addition, higher disease incidence was caused by live seed formulation both in established *Cannabis sativa* plots and in plots inoculated prior to *Cannabis sativa* planting.

In conclusion, this novel method of mycoherbicide application improves penetration of the biocontrol agent into the rhizosphere zone of the target weed. In addition to providing a possible spore delivery mechanism, a beneficial species can also be introduced by serving as the seed carrier, thus providing a hand picked successor species. Thus, live seed delivery systems would offer the added benefit of providing a means to eradicate weeds and re-seed treated areas in a single step.

REFERENCES CITED

Armstrong, G. M., and Armstrong, J. K. 1981. Formae specialis and races of *Fusarium oxysporum* causing wilt diseases. In "Fusarium: Disease, Biology and Taxonomy" (P. E. Nelson, T. A. Toussoun, and R. J. Cook, Eds.) pp. 391–399. Pennsylvania State University Press, University Park. 457 pp.

Ben-Yephet, Y., Reuven, M., and Genzini, A. 1994. Effects of inoculum depth and density on Fusarium wilt in carnations. *Phytopathology* 84: 1393–1398.

Correll, J. C., Klittich, C. J. R., and Leslie, J. F. 1987. Nitrate non-utilizing mutants of *Fusarium oxysporum* and their use in vegetative compatibility tests. *Phytopathology* 77: 1640–1646.

Gracia-Garza, J. A., and Fravel, D. R. 1998. Effect of relative humidity on sporulation of *Fusarium oxysporum* in various formulations and effect of water on spore movement through soil. *Phytopathology*. 88: 544–549.

Grey, W. E., Mathre, D. E. 1988. Evaluation of spring barley for reaction to *Fusarium culmorum* seedling blight and root rot. *Can. J Plant Sci.* 68: 23–30.

Hadar, E., Katan, T., and Katan, J. 1989. The use of nitrate non-utilizing mutants and selective medium for studies of pathogenic strains of *Fusarium oxysporum*. *Plant Disease* 73: 800–803.

Hepple, S. 1960. The movement of fungal spores in soil. *Trans. Brit. Mycol. Soc.* 43:73–79.

Komada, H. 1975. Development of a selective medium for quantitative isolation of *Fusarium oxysporum* from natural soil. *Rev. Plant Prot. Res.* 8: 114–124.

Kraft, J. M., and Haglund, W. A. 1978. A reappraisal of the race classification of *Fusarium oxysporum* f. sp. pisi. *Phytopathology* 68: 273–275.

McCain, A. H., and Noviello, C. 1984. Biological Control of *Cannabis sativa*. Agric. Can. pp. 635–642 Proc. VI Int. Symp. Biol. Contr. Weeds. (E. S. Delfosse, Ed.) Vancouver, Canada.

Noviello, C., and Snyder, W. C. 1962. *Fusarium* Wilt of Hemp. *Phytopathology* 52: 1315–1317.

Tiourebaev, K. S. 1999. Virulence and dissemination enhancement of a mycoherbicide. Ph.D. thesis, Montana State University, Bozeman Tiourebaev, K. S., Pilgeram, A. L., Anderson, T. A., Baizhanov, M. K., Sands, D. C. *Fusarium oxysporum* f. sp. cannabina as promising candidate for biocontrol of Cannabis in Kazakhstan. 1998. (Abstr.) APS.

We claim:

1. A method of dispersing a bioherbicide through a soil profile, comprising:
   combining a live seed with the bioherbicide, which said bioherbicide comprises a live organism, to form a dispersal carrier;
   dispersing the dispersal carrier into an environment having the soil profile; and
   allowing the live seed to germinate, whereby the live organism colonizes the roots of the germinated seed, thereby dispersing the bioherbicide through the soil profile.

2. The method of claim 1, wherein combining comprises coating the seed with the bioactive agent.

3. The method of claim 2, where the seed is further coated with a UV protectant to shield the bioactive agent.

4. The method of claim 1, where a taste repellent is applied to the seed to deter predation.

5. The method of claim 1, where an antibiological agent is applied to the seed to protect it from a microbiological organism.

6. The method of claim 5, where the microbiological organism comprises a bacterium or a fungus.

7. The method of claim 1, where the seed is primed for germination stimulation prior to dispersal.

8. The method of claim 1, where dispersal comprises aerial dispersal.

9. The method of claim 1, where the species of seed selected as the carrier is selected based on criteria that comprise a characteristic of the seed's rhizosphere or a root growth characteristic.

10. The method of claim 9, where the characteristic of the seed's rhizosphere comprises suitability for saprophytic or parasitic growth of the live organism.

11. The method of claim 9, where the root growth characteristic comprises soil penetration or root distribution through the soil profile.

12. The method of claim 1, where the dispersal carrier and/or live organism is traceable.

13. The method of claim 12, where the dispersal carrier and/or live organism is traceable using remote sensing technology.

14. The method of claim 12, where the dispersal carrier and/or live organism is rendered traceable by incorporation of a molecular tag, a biochemical marker, a genetic marker, a physical marker, or a combination thereof.

15. The method of claim 14, further comprising tracing dispersion, growth and/or spread of the dispersal carrier and/or live organism.

16. The method of claim 14, where the dispersal carrier and/or live organism comprises a genetically engineered marker strain.

17. The method of claim 14, further comprising re-isolating a sample of the live organism.

18. The method of claim 2, where the bioactive agent comprises a plurality of fungi, each of which is resistant to at least one fungicide, at a level sufficient to provide the carrier with substantial resistance to a plurality of fungicides.

19. The method of claim 8, further comprising:
   dropping a trackable pseudo-seed to determine deployment information, where such deployment information comprises wind offset, and where the pseudo-seed is equipped with a Global Positioning System receiver and/or Inertial Measurement Unit capable of providing such deployment information, or data from which such deployment information can be calculated.

20. A method of dispersing a bioherbicide comprising:
   combining a live seed with the bioherbicide form a dispersal carrier, wherein the combining comprises coating the seed with the bioherbicide;
   coating the seed with a UV protectant to shield the bioherbicide; and
   dispersing the carrier.

21. A method of dispersing a bioherbicide, comprising:
   combining a live seed with the bioherbicide to form a dispersal carrier;
   applying a taste repellant to the live seed to deter predation; and
   dispersing the carrier.

22. A method of dispersing a bioherbicide, comprising:
   combining a live seed with the bioherbicide to form a dispersal carrier, wherein combining comprises coating the seed with the bioherbicide, and where the bioherbicide comprises a plurality of fungi, each of which is resistant to at least one fungicide, at a level sufficient to provide the carrier with substantial resistance to a plurality of fungicides; and
   dispersing the carrier.

* * * * *